United States Patent [19]

Schmidt et al.

[11] 4,060,549

[45] Nov. 29, 1977

[54] PROCESS FOR PREPARING SULFONIC ACID FLUORIDES

[75] Inventors: Arthur H. Schmidt, Wiesbaden; Reinhard Lantzsch, Cologne; Albrecht Marhold, Leverkusen; Klaus-Friedrich Lehment, Odenthal; Adolf Staffe, Leverkusen, all of Germany

[73] Assignee: Bayer Aktiengesellschaft, Leverkusen, Germany

[21] Appl. No.: 663,881

[22] Filed: Mar. 4, 1976

[30] Foreign Application Priority Data

Mar. 21, 1975 Germany .......................... 2512498

[51] Int. Cl.$^2$ .................. C07C 143/70; C07C 139/00
[52] U.S. Cl. .......................... 260/543 F; 260/515 A; 260/515 M
[58] Field of Search ........... 260/543 F, 515 A, 515 M

[56] References Cited

U.S. PATENT DOCUMENTS

| 2,130,038 | 9/1938 | Schrader et al. | 260/543 F |
| 2,337,532 | 12/1943 | Thomas | 260/543 F |
| 3,560,553 | 2/1971 | Prichard | 260/543 F |
| 3,920,738 | 11/1975 | Martin | 260/543 F |

OTHER PUBLICATIONS

United States Published Patent Application, B504582, Plattner et al., 3-30-76, (9-9-74).

*Primary Examiner*—Norman Morgenstern
*Attorney, Agent, or Firm*—Burgess, Dinklage & Sprung

[57] ABSTRACT

Sulfonic acid fluorides are prepared by reacting sulfonic acid halides with inorganic fluorides in an organic-aqueous phase. The reaction is carried out in the presence of catalytic amounts of an amine or an onium salt.

10 Claims, No Drawings

PROCESS FOR PREPARING SULFONIC ACID FLUORIDES

BACKGROUND

The present invention relates to an improved process for the preparation of sulphonic acid fluorides by reacting sulphonic acid halides with inorganic fluorides.

It is already known to prepare sulphonic acid fluorides from the corresponding sulphonic acid chlorides by halogen exchange. Neutral metal fluorides, alkali metal fluorides or alkali metal hydrogen fluorides are used as the fluorinating agent (see Houben-Weyl, "Methoden der organischen Chemie" ("Methods of Organic Chemistry"), 4th Edition, Volume V/3, page 146). Usually, the reaction is carried out in such a way that the sulphochlorides are reacted with an excess of a 70% aqueous solution of potassium fluoride at the boiling point (W. Davies and J. H. Nick, J. Chem. Soc. (1932), page 483). The yields in which the sulphochlorides are obtained vary greatly. In the case of aromatic sulphonic acid fluorides, yields of between 40 and about 80% are achieved (see Houben-Weyl, Volume V/3, page 147). Aromatic compounds with several sulphochloride groups can also be converted into the corresponding sulphofluorides by prolonged boiling with excess potassium fluoride solution. Thus, yields ranging from 40 to 60% of poly-sulphofluoride compounds are obtained (see Houben-Weyl, Volume V/3, page 148).

However, the known processes for the preparation of sulphonic acid fluorides from sulphonic acid chlorides have considerable disadvantages. Due to the high reaction temperatures required, substantial amounts of energy must be employed when the processes are carried out on an industrial scale. Labile sulphonic acid chlorides, e.g. ethylenesulphochloride, readily undergo hydrolysis or polymerize when subjected to heat and thus are not available for conversion into the corresponding sulphonic acid fluorides (see Houben-Weyl, Volume V/3, page 147).

The present invention provides an economical process which can also be used to chemically labile sulphonic acid fluorides.

SUMMARY

The present invention therefore relates to an improved process for the preparation of sulphonic acid fluorides by reacting sulphonic acid halides with inorganic fluorides, wherein the reaction is carried out in a two-phase system consisting of an organic and an aqueous phase, in the presence of catalytic amounts of an amine or of an onium salt preferably a quarternary ammonium salt.

DESCRIPTION

According to the present invention, sulphonic acid fluorides of all types can be prepared in a simple, gentle and, hence, economical manner. Since the reaction proceeds at room temperature, even those types of sulphonic acid fluorides can be prepared which were not at all attainable, or only at inadequate yields, according to the processes known hitherto.

Amines which can be used for the process according to the invention are primary, secondary or tertiary amines, e.g. methylamine, dimethylamine, ethylamine, diethylamine, n-propylamine, i-propylamine, dipropylamine, n- and i-pentylamine, hexylamine, dodecylamine, octadecylamine, dibutylamine, allylamine, cyclohexylamine, benzylamine, N-methyl-benzylamine, N-methylaniline, N-ethylaniline, diethylaniline, ethanolamine, tetramethylenediamine, 2-dimethylaminoethanol, 2-(2-dimethylamino-ethoxy)-ethanol, 2-diethylaminoethanol, 2-(2-diethylamino-ethoxy)-ethanol, 2-dibutylamino-ethanol, methyl-bis-(2-hydroxyethyl)-amine, bis-(2-hydroxyethyl)-butylamine, tris-[2-(2-hydroxyethoxy)-ethyl]-amine, 3-diethylamino-1-propanol, 1-dimethylamino-2-propanol, 1,1-dimethylamino-2-propanol, methyl-bis-(2-hydroxypropyl)-amine, 1,3-bis-dimethylamino-2-propanol, pyridine, picoline, quinoline, piperidine and morpholine.

Amines of the formula

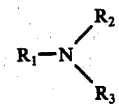

in which $R_1$, $R_2$ and $R_3$ independently of one another represent hydrogen or optionally substituted alkyl, alkenyl, cycloalkyl, aralkyl or aryl or two of the radicals $R_1$, $R_2$ and $R_3$, conjointly with the nitrogen and optionally further hetero-atoms, form a heterocyclic structure, have proved particularly useful.

As $R_1$, $R_2$ $R_3$, possible alkyl radicals are, above all, $C_1$-$C_{18}$ alkyl radicals, preferably $C_1$-$C_8$ alkyl radicals, substituents which may be mentioned being, in particular, the hydroxyl group and lower alkoxy groups, such as the methoxy group, a possible alkenyl radical is the allyl radical, a possible cycloalkyl radical is the cylopentyl radical and above all a cyclohexyl radical which is optionally substituted by hydroxyl or alkyl groups, a possible aralkyl radical is, above all, a benzyl radical, which is optionally substituted by halogen atoms, alkyl radicals or lower alkoxy groups, such as the benzyl, 4-methylbenzyl, 3-chlorobenzyl, 4-methoxybenzyl and α-methylbenzyl radical, and possible aryls are, above all, phenyl radicals which are optionally substituted by lower alkyl or methoxy groups or by halogen atoms.

As heterocyclic structures which can be formed by $R_1$, $R_2$ and/or $R_3$ conjointly with the nitrogen atom and optionally further hetero-atoms, such as oxygen, sulphur or nitrogen, above all, 5-membered and 6-membered heterocyclic structures, such as the pyrrolidine, piperidine or morpholine ring may be mentioned.

Preferably, tertiary amines of the formula I in which $R_1$, $R_2$ and $R_3$ independently of one another represent $C_1$-$C_8$ alkyl radicals, which are optionally substituted by a hydroxyl group or a $C_1$-$C_4$ alkoxy group, are used in the process according to the invention.

Examples of such amines are:
trimethylamine, triethylamine, tri-n-propylamine, tri-n-butylamine, tri-n-pentylamine, tri-i-propylamine, tri-i-butylamine, tri-i-pentylamine, tri-n-hexylamine, tris-(2-hydroxyethyl)-amine and tris-(2-hydroxypropyl)-amine.

Onium salts which can be used are, above all, ammonium or phosphonium salts, especially quaternary ammonium salts. The onium salts correspond to the formula

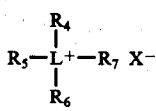

in which

L represents nitrogen or phosphorus, $R_4$, $R_5$, $R_6$ and $R_7$ denote independently of one another optionally substituted alkyl, aralkyl or aryl or alternatively a heterocyclic structure by combining two adjacent radicals amongst $R_4$, $R_5$, $R_6$ and $R_7$ and including the central atom L and optionally further heteroatoms, $X^-$ represents a halide, cyanide or hydroxyl ion.

As $R_4$, $R_5$, $R_6$ and $R_7$, alkyl radicals which may be mentioned are, above all, $C_1-C_{18}$ alkyl radicals, such as the methyl, ethyl, propyl, butyl, heptyl, hexyl, dodecyl and octadecyl radical, aralkyl radicals which may be mentioned are benzyl radicals which are optionally substituted by $C_1-C_4$ alkyl radicals or methoxy groups or halogen and aryl radicals which may be mentioned are, above all, phenyl radicals which are substituted by $C_1-C_4$ alkyl or $C_1-C_2$ alkoxy groups or halogen atoms.

Examples of heterocyclic structures which can be formed by combining two adjacent radicals amongst $R_4$, $R_5$, $R_6$ and $R_7$, with the central atom L and optionally further heretoatoms, such as oxygen, sulphur or nitrogen, are, above all, 5-membered and 6-membered heterocyclic structures, such as the pyrrolidine, piperidine or morpholine ring.

Examples of onium salts to be used according to the invention e.g.: tetraethylammonium chloride, tetrabutylammonium bromide, tetrabutylammonium iodide, triethyl-benzyl-ammonium chloride, methylbutylpiperidinium iodide, tetraethylammonium bromide, tetrabutylammonium chloride, benzyl-methylpiperidinium iodide, tetraethylammonium cyanide, benzyltrimethylammonium hydroxide, benzyltrimethylammonium cyanide, triphenylbenzylphosphonium bromide and benzyldodecyldimethylammonium chloride.

Quaternary ammonium salts of the formula II, in which $R_4$ and $R_5$ independently of one another represent $C_1-C_4$ alkyl and $R_6$ represents $C_1-C_4$ alkyl or benzyl and $R_7$ represents $C_1-C_{14}$ alkyl or phenyl or $R_4$ and $R_5$, conjointly with the nitrogen atom, form a 5-membered or 6-membered heterocyclic structure, have proved particularly useful.

The amount of catalyst can vary within wide limits. In general, 0.1 to 10% by weight, preferably 0.3 to 5% by weight, based on the weight of the sulphonic acid halide, have proved suitable. The catalyst can be added to the reaction system in various ways. It may be introduced together with the aqueous and/or organic phase or may also be introduced as such after mixing the two phases. The catalyst may also be employed as a solution in a solvent.

Sulphonic acid halides used as starting materials for the process according to the invention can be characterised by the general formula

in which

X represents bromine or, preferably, chlorine and

R denotes any desired organic radical, which is bonded via a carbon atom to the $-SO_2X$ group.

For example, R may denote a straight-chain, branched or cyclic hydrocarbon radical or a hydrocarbon radical which simultaneously contains chain and cyclic structural elements. The hydrocarbon radical may be saturated, unsaturated or aromatic. The radical R may contain hetero-atoms, for example fluorine, chlorine, bromine, iodine, oxygen, sulphur, nitrogen and/or phosphorus atoms, one or more of these hetero-atoms being arranged in and/or on the ring or in and/or on the chain. The radical R may also contain further $-SO_2-X$ groups, in which X has the abovementioned meaning. In this case, X is exchanged by fluorine in these groups, too; hence the process of the invention allows to prepare poly-sulphonic acid fluorides, for example disulphonic acid fluorides. The radical R preferably contains 1-28 C atoms, preferentially 1-14 C atoms.

Examples of sulphonic acid halides, which may be employed in the process according to the invention, are: methanesulphonic acid chloride, chloromethanesulphonic acid chloride, dichloromethanesulphonic acid chloride, trichloromethanesulphonic acid chloride, ethanesulphonic acid chloride, vinylsulphonic acid chloride, chloroethanesulphonic acid chloride, propanesulphonic acid chloride, butanesulphonic acid chloride, chlorobutanesulphonic acid chloride, pentanesulphonic acid chloride, hexanesulphonic acid chloride, heptanesulphonic acid chloride, octanesulphonic acid chloride, dodecanesulphonic acid chloride, stearic sulphonic acid chloride, a statistically substituted mixture of alkane-sulphochlorides (industrial name: Mersol), dimethylvinylsulphonic acid chloride, methallylsulphonic acid chloride, phenylmethanesulphonic acid chloride, 1,2-phenylenebis-methanesulphonic acid chloride, trichlorovinylsulphonic chloride, benzenesulphonic acid chloride, chlorobenzenesulphonic acid chloride, dichlorobenzenesulphonic acid chloride, bromobenzenesulphonic acid chloride, fluorobenzenesulphonic acid chloride, iodobenzenesulphonic acid chloride, nitrobenzenesulphonic acid chloride, dinitrobenzenesulphonic acid chloride, toluenesulphonic acid chloride, trifluoromethylbenzenesulphonic acid chloride, naphthalene-1-sulphonic acid chloride, naphthalene-2-sulphonic acid chloride, methoxybenzenesulphonic acid chloride, acetaminobenzenesulphonic acid chloride, chloronitrobenzene sulphonic acid chloride, nitrotoluenesulphonic acid chloride, dinitrotoluenesulphonic acid chloride, tetralenesulphonic acid chloride, nitronaphthalenesulphonic acid chloride, biphenylsulphonic acid chloride, pyrenesulphonic acid chloride, benzenedisulphonic acid chloride, nitrobenzenedisulphonic acid chloride, naphthalenedisulphonic acid chloride, dinitronaphthalenedisulphonic acid chloride, biphenyldisulphonic acid chloride, naphthalenetrisulphonic acid chloride, naphthalenetetrasulphonic acid chloride, diphenylsulphone-disulphonic acid chloride, diphenylsulphone-disulphonic acid chloride, diphenylethyldisulphonic acid chloride, nitroanisolesulphonic acid chloride, anthraquinonesulphonic acid chloride, benzoic acid sulphonic acid chloride, chlorobenzoic acid sulphonic acid chloride, benzoic acid disulphonic acid chloride, phthalic acid sulphonic acid chloride and terephthalic acid sulphonic acid chloride.

The sulphonic acid chlorides used as starting compounds frequently still contain larger or lesser amounts of hydrogen chloride originating from their preparation, usually have to be removed before further chemical reaction. However, even these crude sulphonic acid chlorides containing hydrogen chloride can be employed in the process according to the invention if the hydrogen chloride is bonded by adding amines. The ammonium salt thus formed acts as a catalyst in the subsequent chlorine/fluorine exchange reaction, simultaneously.

Inorganic fluorides which can be used for the process according to the invention are all salts which split off fluoride ions in aqueous solution; e.g.

metal salts of hydrofluoric acid, such as alkali metal fluorides, alkali metal hydrogen fluorides, or complex alkali metal fluorides, such as cryolite, potassium borofluoride and sodium hexafluorosilicate, as well as ammonium fluoride and ammonium hydrogen fluoride. Alkali metal fluorides and alkali metal hydrogen fluorides, especially sodium fluoride, potassium fluoride, sodium hydrogen fluoride and potassium hydrogen fluoride, are preferably used; mixtures of different fluorides can also be employed.

In the process according to the invention, the organic phase is formed by the sulphonic acid halide and/or sulphonic acid fluoride or by the solution of the sulphonic acid halide and/or sulphonic acid fluoride in an organic solvent which is inert under the reaction conditions and which, at least to a substantial extent, is immiscible with water.

Examples which may be mentioned of organic solvents which are inert under the reaction conditions and which, at least to a substantial extent, are immiscible with water are hydrocarbons, such as benzine, petroleum ether, cyclohexane, benzene, toluene and xylene; chlorinated hydrocarbons, such as chlorobenzene, dichlorobenzene, methylene chloride, chloroform, carbon tetrachloride, 1,2-dichloroethane, 1,2-dichloropropane, tetrachloroethane and trichloroethylene; and ethers, such as diisopropyl ether. Preferably, methylene chloride, chloroform or diethyl ether are used. The organic phase may also consist of a mixture of several solvents.

The amount of organic solvents used may vary within wide limits, e.g. from 0.01 kg to 20 kg per kg of acid halide.

In the process according to the invention, the aqueous phase is formed by the aqueous solution of the inorganic fluoride. The concentration of the fluoride in the aqueous phase may vary within wide limits; in general, concentrations of from 10 to 80% by weight of fluoride have proved useful. It has proved advantageous to work with solutions as concentrated as possible. Under certain circumstances, these solutions may still contain undissolved fluoride. When the reaction is complete, the aqueous phase also contains the salts formed during the reaction and/or small amounts of sulphonic acid.

The amounts of inorganic fluoride are so apportioned that there is at least one equivalent of fluoride per one equivalent of acid halide. The use of 1.1 to 4 equivalents of fluoride, preferably 1.1 to 3 equivalents, per equivalent of acid halide has proved particularly advantageous.

The process according to the invention may be carried out, for example, as follows: the sulphonic acid halide or the solution thereof in an inert solvent which, at least substantially, is immiscible with water, is stirred with the aqueous solution of the fluoride and the catalyst. It is also possible to add the fluoride gradually in several portions instead of all at once. The sulphonic acid halide reacts to give the corresponding sulphonic acid fluoride; at the same time the corresponding metal halide is formed from the metal fluoride employed and, in some cases, small amounts of sulphonic acid are formed by hydrolysis. The sulphonic acid fluoride formed is then isolated from the reaction mixture. Any starting materials (sulphonic acid halides and/or fluorides) which may not have reacted and any solvent which may be present can be used again.

The process according to the invention is not restricted to any specific temperature. In general, it is carried out at temperatures of from $-10°$ to $+80°$ C, preferably from $0°$ to $+60°$ C. If the sulphonic acid halide is employed as a solution in an organic solvent, a solvent which has a boiling point above the desired reaction temperature is preferably chosen.

The process according to the invention may be carried out under normal pressure, reduced pressure or excess pressure. It is preferably carried out under normal pressure.

The reaction period depends on the reactivity of the acid halide employed and is between 15 minutes and 10 hours. In general it is from 30 minutes to 6 hours.

The procedure followed for working up the reaction mixture obtained depends on the properties of the sulphonic acid halide employed and of the sulphonic acid fluoride formed. If, for example, a readily volatile sulphonic acid fluoride is prepared and the reaction is carried out without using a solvent, the sulphonic acid fluoride formed may already be withdrawn in the gaseous form during the reaction and collected as a gas or, after condensation, as a liquid.

In the case of non-volatile sulphonic acid fluorides, two phases, the organic phase and the aqueous phase, are obtained after the reaction is complete. Both have to be worked up separately. If the reaction of the sulphonic acid halide has been carried out without the addition of solvents, phase separation can be incomplete. In such cases it is appropriate to add an organic solvent, which, at least substantially, is immiscible with water, separation of the reaction mixture into two phases being achieved in this way. The organic phase contains the sulphonic acid fluoride formed as well as, in some cases, unreacted sulphonic acid halide, organic solvents, small amounts of sulphonic acid formed by hydrolysis, small amounts of catalyst and/or small amounts of water. Advantageously, the organic phase is first dired in a manner which is in itself known, for example by adding a water-binding agent, such as anhydrous sodium sulphate magnesium sulphate or calcium chloride. The sulphonic acid fluoride is isolated from the dried solution with the aid of processes which are in themselves known, for example by fractional distillation. When the organic phase still contains unreacted sulphonic acid halide, this may also be separated and recycled into the reaction.

The aqueous phase which contains the salt formed in the reaction as well as any unreacted or excess fluoride, small amounts of sulphonic acid formed by hydrolysis and small amounts of the catalyst, is generally discarded. However, in order to avoid an unnecessary load on the effluent and to be able to recycle any re-usable materials which may be present in the aqueous phase, it is also possible to work up the aqueous phase. This can be effected, for example, by fractional crystallisation. In this case, at least part of the salt precipitates in such a way that it can be filtered off and then be used for other purposes. The solution which remains after separating the salt can be re-used in the process according to the invention, after adding fresh fluoride if necessary. Any salt which has not been completely separated off or small amounts of sulphonic acid, which may still be contained in the aqueous phase, do not interfere when the aqueous phase is re-used.

The process according to the invention can be carried out both discontinuously and continuously. In the case of the continuous procedure it is advantageous to recycle all of the reusable reactants and auxiliaries.

In a particular embodiment of the process according to the invention, the procedure is as follows: the sulphonic acid chloride is dissolved in a solvent, for example methylene chloride; then the aqueous solution of the fluroide (equivalent ratio of sulphochloride: metal fluoride = 1:1.5-2) is added whilst stirring. 0.3 to 5% by weight, based on the weight of the sulphonic acid chloride, of catalyst, for example triethylamine, are then added. The mixture is stirred for about 4 hours at room temperature; the reaction is slightly exothermic. When the reaction is complete, the two phases are separated. The sulphonic acid fluoride formed is separated from the organic phase, after drying with anhydrous sodium sulphate, by fractionel distillation. Any unreacted sulphonic acid chloride which remains is combined with the solvent separated during the fractional distillation, and the mixture is re-used after adding fresh sulphonic acid chloride. If it has not already precipitated in a solid form during the reaction, the salt formed is induced to precipitate by fractional crystallisation and is filtered off and removed. The remaining residue of the aqueous phase is re-employed after adding fresh fluoride.

The sulphonic acid fluorides which can be prepared by the process according to the invention are of interest in diverse industrial fields. Thus, German Pat. No. 2,103,613 discloses the use of substituted benzenesulphonic acid fluorides as an additive to coatings which provide protection against attack by fungi. Other substituted benzenesulphonic acid fluorides serve as fungicides (see Japanese Application No. 70/10,358). According to U.S. Pat. No. 3,635,964, sulphonic acid fluorides exhibit a bactericidal, fungicidal, herbicidal or insecticidal action. The use of aromatic sulphonic acid fluorides as soil fungicides is described in U.S. Pat. No. 3,658,965.

EXAMPLE 1

A solution of 106 g (0.6 mol) of benzenesulphonic acid chloride in 200 ml of ether is treated, at room temperature, first with 1.5 g of tetrabutylammonium bromide and, after stirring for two minutes, with a solution of 87 g (1.5 mols) of potassium fluoride in 90 ml of water. The reaction mixture is stirred for 4 hours at room temperature.

The two liquid phases are then decanted off from the potassium chloride which has precipitated out, the potassium chloride is washed with ether and the washing ether is combined with the liquid already decanted. The organic phase is then separated from the aqueous phase and dried over sodium sulphate.

After distilling off the ether, 85.8 g of a liquid residue are obtained, which according to gas chromatographic analysis contains up to 98.5% of benzenesulphonic acid fluoride.

Distillation of the residue gives 76 g of benzenesulphonic acid fluoride (purity: 99.9%; yield: 81% of theory).

EXAMPLE 2

A solution of 102 g (0.6 mol) of benzenesulphonic acid chloride in 250 ml of methylene chloride is treated, at room temperature, first with 2 ml of phenyl-benzyl-dimethylammonium chloride and then, after stirring briefly, with a solution of 116 g (2 mols) of potassium fluoride in 120 ml of water. The reaction mixture is stirred for 6 hours at room temperature.

The reaction mixture is worked up as described in Example 1. 86.4 g of a liquid residue, which according to gas chromatographic analysis contains up to 91.4% of benzenesulphonic acid fluoride, are obtained.

EXAMPLE 3

A solution of 106 g (0.6 mol) of benzenesulphonic acid chloride in 250 ml of methylene chloride is treated with 2 g of benzyltriethylammonium chloride and a solution of 87 g (1.5 mols) of potassium fluoride in 60 ml of water. The reaction mixture is stirred for 4 hours at room temperature.

The reaction mixture is worked up as described in Example 1. 82.3 g of a liquid residue, which according to gas chromatographic analysis contains up to 96.6% of benzenesulphonic acid fluoride, are obtained.

EXAMPLE 4

A solution of 106 g (0.6 mol) of benzenesulphonic acid chloride in 250 ml of methylene chloride is treated with 2 g of phenyl-benzyl-dimethyl-ammonium chloride and a solution of 94 g (1.2 mols) of potassium hydrogen fluoride in 170 ml of water. The reaction mixture is stirred for 4 hours at room temperature.

The reaction mixture is worked up as described in Example 1 to yield 85.9 g of a liquid residue, which according to gas chromatographic analysis has the following composition: 82.1% of benzenesulphonic acid fluoride, 15.6% of benzenesulphonic acid chloride and 2.3% of other substances.

EXAMPLE 5

A solution of 106 g (0.6 mol) of benzenesulphonic acid chloride in 250 ml of methylene chloride is treated at room temperature with a solution of 94 g (1.2 mols) of potassium hydrogen fluoride in 180 ml of water. A solution of 5 ml of triethylamine in 14 ml of methylene chloride is added dropwise to this mixture at 25° to 40° C. The reaction mixture is stirred for 4 hours. The two phases are then separated. The organic phase is washed with twice 50 ml of 2 N HCl and then dried over sodium sulphate. After removing the methylene chloride in a rotary evaporator, the remaining 71.4 g of a liquid residue, according to gaschromatographic analysis, have the following composition: 82.1% of benzenesulphonic acid fluoride, 15.9% of benzenesulphonic acid chloride and 2.0% of other substances.

EXAMPLE 6

A solution of 106 g (0.6 mol) of benzenesulphonic acid chloride in 200 ml of diethyl ether is treated with 1.5 g of tetrabutylammonium bromide and a solution of 46.5 g (0.8 mol) of potassium fluoride in 45 ml of water. On mixing the phases, the reaction temperature rises to 32° C. After stirring for six hours, the reaction mixture is worked up as described in Example 1.

89.8 g of a pale yellow liquid, which according to gas chromatographic analysis consists to the extent of 98.2% of benzenesulphonic acid fluoride, are obtained.

Distillation of the liquid gives 82.2 g of benzenesulphonic acid fluoride (purity: 99.9%; yield 87%).

EXAMPLE 7

A solution of 106 g (0.6 mol) of benzenesulphonic acid chloride in 200 ml of dimethyl ether is treated with 1.5 g of tetrabutylammonium bromide and a solution of 37 g (1 mol) of ammonium fluoride in 50 ml of water. The reaction mixture is stirred for 4 hours at room temperature and then worked up as described in Example 1.

This gives 93.8 g of a liquid which, according to gas chromatographic analysis, has the following composition: 74.8% of benzenesulphonic acid fluoride, 24.4% of benzenesulphonic acid chloride and 0.8% of other substances.

EXAMPLE 8

A solution of 106 g (0.6 mol) of benzenesulphonic acid chloride in 200 ml of diethyl ether is treated with 1.5 g of tetrabutylammonium bromide and a solution of 57 g (1 mol) of ammonium hydrogen fluoride in 80 ml of water. The reaction mixture is stirred for 5 hours at room temperature and then worked up as described in Example 1.

This gives 85.5 g of a liquid which, according to gas chromatograhic analysis, has the following composition: 74.8% of benzenesulphonic acid fluoride, 23.6% of benzenesulphonic acid chloride and 1.6% of other substances.

EXAMPLE 9

A solution of 106 g (0.6 mol) of benzenesulphonic acid chloride in 400 ml of diethyl ether is treated with 1.5 g of tetrabutylammonium bromide and a solution of 78 g (1 mol) of potassium hydrogen fluoride in 140 ml of water. The reaction mixture is stirred for 5 hours at room temperature and then worked up as described in Example 1.

This gives 90.5 g of a liquid which, according to gas chromatographic analysis has the following composition: 91.9% of benzenesulphonic acid fluoride, 7.3% of benzenesulphonic acid chloride and 0.8% of other substances.

EXAMPLE 10

A solution of 114 g (0.6 mol) of 4-toluenesulphonic acid chloride in 200 ml of diethyl ether is first treated with 1.5 g of tetrabutylammonium bromide and a solution of 87 g (1.5 mols) of potassium fluoride in 90 ml of water is then added dropwise at room temperature, whilst stirring. After stirring for five hours, the reaction mixture is worked up as described in Example 1.

This given 94 g of a pale yellow liquid which, according to gas chromatograhic analysis, has the following composition: 71.2% of 4-toluenesulphonic acid fluoride, 27.9% of 4-toluenesulphonic acid chloride and 0.9% of other substances.

EXAMPLE 11

A solution of 127 g (0.6 mol) of 4-chlorobenzenesulphonic acid chloride in 250 ml of chloroform is first treated with a solution of 69.5 g (1.2 mols) of potassium fluoride in 70 ml of water and a solution of 2 g of benzyltriethylammonium chloride in 5 ml of water is then added dropwise, whilst stirring. The temperature rises to 35° C. After stirring for six hours, the reaction mixture is worked up as described in Example 1.

This gives 105.5 g of a solid substance which, after recrystallisation from petroleum ether, melts at 49° C. According to gas chromatographic analysis, the substance consists to the extent of 99.9% of 4-chlorobenzenesulphonic acid fluoride (yield: 90%).

EXAMPLE 12

A solution of 127 g (0.6 mol) of 3-chlorobenzenesulphonic acid chloride in 250 ml of methylene chloride is first treated with a solution of 69.5 g (1.2 mols) of potassium fluoride in 70 ml of water and a solution of 2 g of benzyltriethylammonium chloride in 5 ml of water is then added dropwise, whilst stirring. During the dropwise addition of the catalyst the temperature of the reaction mixture rises to 34° C. After stirring for six hours, the reaction mixture is worked up as described in Example 1.

This gives 117 g of a liquid which, according to gas chromatographic analysis, consists to the extent of 97.2% of 3-chlorobenzenesulphonic acid fluoride (yield: 97%).

EXAMPLE 13

A solution of 114 g (0.6 mol) of 2-toluenesulphonic acid chloride in 250 ml of methylene chloride is first treated with a solution of 69.5 g (1.2 mols) of potassium fluoride in 70 ml of water and a solution of 2 g of benzyltriethylammonium chloride in 5 ml of water is then added dropwise, whilst stirring. After stirring for six hours, the reaction mixture is worked up as described in Example 1.

This gives 100 g of a clear liquid which, according to gas chromatographic analysis, consists to the extent of 98% of 2-toluenesulphonic acid fluoride.

EXAMPLE 14

A solution of 122.7 g (0.5 mol) of 3,4-dichlorobenzenesulphonic acid chloride in 250 ml of methylene dchloride is first treated, at room temperature, with a solution of 58 g (1 mol) of potassium fluoride in 60 ml of water and a solution of 1.5 g of benzyltriethylammonium chloride in 5 ml of water is then added dropwise, whilst stirring. During the dropwise addition of the catalyst, the temperature rises within a short time to 40° C. After stirring for six hours, the reaction mixture is worked up as described in Example 1.

This gives 106.5 g of a pale yellow liquid which, according to gas chromatographic analysis, consists to the extent of 97.5% of 3,4-dichlorobenzenesulphonic acid fluoride.

EXAMPLE 15

A solution of 110.7 g (0.5 mol) of 2-nitrobenzenesulphonic acid chloride in 250 ml of methylene chloride is first treated, at room temperature, with a solution of 58 g (1 mol) of potassium fluoride in 60 ml of water and a solution of 1 g of benzyltriethylammonium chloride in 5 ml of water is then added dropwise, whilst stirring. During the addition of the catalyst, the temperature of the reaction mixture rises to about 50° C. After stirring for six hours, the reaction mixture is worked up as described in Example 1.

97.7 g of yellowish crystals are obtained. After recrystallisation from petroleum ether/methylene chloride, 87.4 g of 2-nitrobenzenesulphonic acid fluoride, which is pure according to gas chromatography, are obtained (yield: 85% of theory).

EXAMPLE 16

A solution of 76.5 g (0.4 mol) of 4-chlorobutanesulphonic acid chloride in 150 ml of methylene chloride is treated, at room temperature, with a solution of 23.1 g (0.4 mol) of potassium fluoride in 50 ml of water and 3 ml of triethylamine. After stirring for 2 hours, the organic phase is separated off and dried over sodium sulphate. After removing the methylene chloride in a rotary evaporator, the residue is subjected to fractional distillation in a high vacuum.

This gives 6 g of 4-chlorobutanesulphonic acid chloride and 52 g of 4-chlorobutanesulphonic acid fluoride (boiling point$_{0.5}$: 60 – 68° C; yield: 81%).

If the reaction is carried out without the addition of triethylamine, only 14 g of 4-chlorobutanesulphonic acid fluoride are obtained.

EXAMPLE 17

A solution of 69.6 g (1.2 mols) of potassium fluoride in 160 ml of water is treated with 212 g (1 mol) of n-octanesulphonic acid chloride. 20 g of tris-(2-hydroxypropyl)-amine are then metered into this mixture at 50° C. The reaction mixture is kept at 50° C for 2 hours. After cooling, the organic phase is separated off, dried with sodium sulphate and then subjected to fractional distillation in vacuo.

This gives 187 g of n-octanesulphonic acid fluoride (boiling point$_9$: 102° C; yield: 95%).

EXAMPLE 18

A solution of 95.25 g (0.5 mol) of phenylmethanesulphonic acid chloride in 400 ml of methylene chloride is treated with a solution of 34.8 g (0.6 mol) of potassium fluoride in 80 ml of water. 10 g of triethylamine are added dropwise to the mixture at 25° C. After stirring for 3 hours at room temperature, the organic phase is separated off, dried with sodium sulphate and then freed from the solvent in a rotary evaporator. The residue is distilled in a high vacuum.

This gives 84.5 g of phenylmethanesulphonic acid fluoride (boiling point$_{0.5}$: 80 – 85° C; yield: 97%).

EXAMPLE 19

A solution of 51 g (1 mol) of potassium fluoride in 100 ml of water is first treated with 10 ml of a 50% strength aqueous solution of benzyldodecyldimethylammonium chloride and a solution of 95.25 g (2.5 mols) of phenylmethanesulphonic acid chloride in 400 ml of methylene chloride is then added, at 25° C, in the course of 30 minutes. After stirring for three hours, the organic phase is separated off, dried with sodium sulphate and freed from the solvent in vacuo.

The residue is recrystallised from petroleum ether. This gives 68 g of phenylmethanesulphonic acid fluoride (melting point: 90° C; yield: 77%).

EXAMPLE 20

A solution of 23.2 g (0.4 mol) of potassium fluoride in 100 ml of water is treated successively with 5 of tris-(2-hydroxypropyl)-amine and then with a solution of 38.1 g (0.2 mol) of phenylmethanesulphonic acid chloride in 150 ml of methylene chloride. After stirring for 2 hours at 25° C, the organic phase is separated off and dried with sodium sulphate.

The residue which remains after distilling off the solvent is distilled in a high vacuum. This gives 31 g (89%) of phenylmethanesulphonic acid fluoride (boiling point$_{0.4}$: 81 – 86° C).

EXAMPLE 21

A solution of 190.5 g (1 mol) of p-toluenesulphonic acid chloride in 300 ml of toluene is treated with 5 g of tetrabutylphosphonium chloride and a solution of 69.6 g (1.2 mols) of potassium fluoride in 160 ml of water. The reaction mixture is heated at 40° C for 1 hour, whilst stirring, and then cooled to room temperature. The organic phase is separated off and the toluene is distilled off from this phase in vacuo. The residual oil solidifies after some time and is dried on clay.

This gives 165 g (95% of theory) of p-toluenesulphonic acid fluoride (melting point: 42 – 43° C).

EXAMPLE 22

25 g of potassium fluoride are dissolved in 25 ml of water, 3 g of triephenylisopropylphosphonium bromide are added to the solution and the entire mixture is stirred for about 20 minutes. A solution of 42.5 g (0.2 mol) of n-octanesulphonic acid chloride in 120 ml of chloroform is then added slowly dropwise. The temperature of the reaction mixture is 27 – 30° C. After stirring for 4 hours, the organic phase is separated off, dried with sodium sulphate and freed from chloroform by distillation in vacuo.

According to gas chromatographic analysis, the residue (39 g) has the following composition: 4% of chloroform, 93% of n-octanesulphofluoride and 3% of n-octanesulphochloride.

This corresponds to a yield of 92% of theory.

EXAMPLE 23

A mixture consisting of 156.6 g (1 mol) of n-butanesulphonic acid chloride and a solution of 69.6 g (1.2 mols) of potassium fluoride in 160 ml of water is treated with 10 g of triphenylbenzylphosphonium chloride. After stirring for 3 hours at room temperature, the crude n-butanesulphonic acid fluoride is separated off and subjected to fractional distillation.

This gives 122 g (87% of theory) of n-butanesulphonic acid fluoride (boiling point$_{10}$: 45 – 48° C).

What is claimed is:

1. In a process for preparing sulfonic acid fluorides by reacting sulfonic acid halides with inorganic fluorides in an organic aqueous phase, the improvement comprising carrying out the reaction of a sulfonic acid halide having the structure

R—SO$_2$—X in which
  X is bromine or chlorine and
  R is a straight-chain, branched or cyclic hydrocarbon radical of 1–28 C atoms which can simultaneously contain chain and cyclic structural elements, saturated, unsaturated or aromatic, which can be further substituted by —SO$_2$X—groups, fluorine, chlorine, bromine, iodine, oxygen, sulphur, nitrogen and/or phosphorus, one or more of which being arranged in and/or on a ring or in and/or on a chain with an inorganic fluoride in a water immiscible inert organic solvent in the presence of a catalytic amount of an amine having the structure

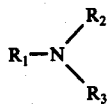

in which
R$_1$, R$_2$, and R$_3$ are independently selected from the group consisting of alkyl, alkyl substituted by hydroxy or lower alkoxy, alkenyl, cycloalkyl, cycloalkyl substituted by hydroxy or alkyl, aralkyl, aralkyl substituted by halogen, alkyl or lower alkoxy, aryl, aryl substituted by lower alkyl, methoxy or halogen, or conjointly R$_1$, R$_2$ and/or R$_3$ combined with the nitrogen and/or additional hetero-atoms selected from the group consisting of oxygen, sulphur or nitrogen, form a 5-membered or 6-membered heterocyclic structure, or in the presence of a catalytic amount of an onium salt having the formula

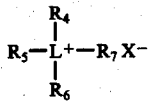

in which
L is nitrogen or phosphorous; R$_4$, R$_5$, R$_6$ and R$_7$ are independently selected from the group consisting of alkyl, aralkyl substituted by C$_1$-C$_4$ alkyl, methoxy or halogen, aryl, and aryl substituted by C$_1$-C$_4$ alkyl, C$_1$-C$_2$ alkoxy or halogen, or alternatively, two adjacent radicals amongst R$_4$, R$_5$, R$_6$ and R$_7$ and including the central atom L, form a 5 or 6-membered heterocyclic structure which can additionally contain a further hetero atom selected from the group consisting of oxygen, sulfur or nitrogen; and X$^-$ is a halide, cyanide or hydroxyl ion.

2. Process of claim 1 wherein R$_1$, R$_2$ and R$_3$ independently of one another represent C$_1$ - C$_8$ alkyl which is optionally substituted by a hydroxyl group or a C$_1$ - C$_4$ alkoxy group.

3. Process of claim 1 wherein L represents nitrogen.

4. Process of claim 1 wherein
R$_4$ and R$_5$ independently of one another represent C$_1$-C$_4$ alkyl and
R$_6$ represents C$_1$-C$_4$ alkyl or benzyl and
R$_7$ represents C$_1$-C$_{14}$ alkyl or phenyl or
R$_4$ and R$_5$, conjointly with the nitrogen atom, form a 5-membered or 6-membered heterocyclic structure.

5. Process of claim 1 wherein the catalyst is employed in amounts of from 0.1 to 10% by weight, based on the weight of the acid halide.

6. Process of claim 1 wherein the catalyst is employed in amounts of from 0.3 to 5% by weight, based on the weight of the acid halide.

7. Process of claim 1 carried out at temperatures of from 0° to +60° C.

8. Process of claim 2 wherein
R$_4$ and R$_5$ independently of one another represent C$_1$-C$_4$ alkyl and
R$_6$ represents C$_1$-C$_4$ alkyl or benzyl and
R$_7$ represents C$_1$-C$_{14}$ alkyl or phenyl or
R$_4$ and R$_5$, conjointly with the nitrogen atom, form a 5-membered or 6-membered heterocyclic structure.

9. Process of claim 8 wherein the catalyst is employed in amounts of from 0.1 to 10% by weight, based on the weight of the acid halide.

10. Process of claim 9 carried out at temperatures of from 0° to +60° C.

* * * * *